(12) United States Patent
O'Connor et al.

(10) Patent No.: US 8,168,682 B2
(45) Date of Patent: *May 1, 2012

(54) PERSONAL PRODUCT BAR COMPOSITIONS COMPRISING CRYSTALLINE WAX STRUCTURED PREMIX OR DELIVERY VEHICLE

(75) Inventors: Stephen M. O'Connor, New York, NY (US); Birnur Aral, West New York, NJ (US); John Richard Nicholson, Ramsey, NJ (US); Quynh Pham, Murray Hill, NJ (US); John R. Glynn, Jr., Westfield, NJ (US); Alexander Lips, Edgewater, NJ (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 779 days.

This patent is subject to a terminal disclaimer.

(21) Appl. No.: 11/669,255

(22) Filed: Jan. 31, 2007

(65) Prior Publication Data

US 2007/0129272 A1   Jun. 7, 2007

Related U.S. Application Data

(62) Division of application No. 10/443,395, filed on May 22, 2003, now abandoned.

(51) Int. Cl.
| | |
|---|---|
| *A01N 27/00* | (2006.01) |
| *A01N 25/00* | (2006.01) |
| *A61K 31/01* | (2006.01) |
| *A61K 47/00* | (2006.01) |
| *A61K 8/02* | (2006.01) |
| *A61Q 19/10* | (2006.01) |
| *C11D 17/00* | (2006.01) |

(52) U.S. Cl. .................. 514/762; 514/785; 510/141

(58) Field of Classification Search ................. 514/762, 514/785; 510/141
See application file for complete search history.

(56) References Cited

U.S. PATENT DOCUMENTS

| 3,969,259 | A | * | 7/1976 | Lages .................. 510/101 |
| 5,661,189 | A | | 8/1997 | Grieveson et al. |
| 5,674,511 | A | | 10/1997 | Kacher et al. |
| 5,804,540 | A | | 9/1998 | Tsaur et al. |
| 5,804,640 | A | | 9/1998 | Laura et al. |
| 5,817,609 | A | | 10/1998 | He et al. |
| 6,458,751 | B1 | | 10/2002 | Abbas et al. |
| 6,923,975 | B2 | | 8/2005 | Aronson et al. |
| 2003/0049282 | A1 | | 3/2003 | Aronson et al. |
| 2003/0054019 | A1 | | 3/2003 | Aronson et al. |
| 2004/0234467 | A1 | | 11/2004 | Ananthapadmanabhan et al. |
| 2004/0234470 | A1 | | 11/2004 | Zhang et al. |
| 2004/0234558 | A1 | | 11/2004 | O'Connor et al. |

FOREIGN PATENT DOCUMENTS

WO   01/13871 A1   3/2001

OTHER PUBLICATIONS

European Search Report Application No. EP 04 25 3008 dated Sep. 20, 2004.
U.S. Appl. No. 10/443,394, filed May 22, 2003 to Kerschner et al. cited by Examiner in parent appl'n.

* cited by examiner

*Primary Examiner* — Sreeni Padmanabhan
*Assistant Examiner* — Kendra D Carter
(74) *Attorney, Agent, or Firm* — Ronald A. Koatz

(57) ABSTRACT

The present invention relates to compositions comprising a structured benefit agent pre-mix or delivery vehicle comprising benefit agent structured with crystalline materials, as defined, which when separately prepared and combined after preparation, provides enhanced delivery of benefit agent from a personal product bar carrying composition into which the premix is added. The use of structured benefit agent also enhances delivery of separate benefit agents in the premix (which may or may not be structured) and of separate benefit agents added separately from the premix.

3 Claims, 4 Drawing Sheets

PERSONAL PRODUCT BAR COMPOSITIONS COMPRISING CRYSTALLINE WAX STRUCTURED PREMIX OR DELIVERY VEHICLE

The present application is a divisional application of U.S. Ser. No. 10/443,395, filed May 22, 2003.

FIELD OF THE INVENTION

The present invention comprises a structured premix or "delivery vehicle" composition designed to enhance delivery (e.g., via enhanced deposition) of hydrophobic benefit agent(s), for example, moisturizing oils, from personal product bar compositions. When the structured benefit agent composition is separately prepared and combined with the personal product composition (preferably, while structured, the premix composition is still in a molten or liquid state although it can also be in a semi-molten or solid state), a personal product bar composition is provided which yields enhanced delivery of the benefit agent(s).

It should be noted that not only the benefit agent which is structured will benefit from enhanced delivery, but also benefit agents which are separately found in the composition (e.g., entrapped within a network formed by the structured benefit agent or added separately and not as part of the premix) also may have enhanced delivery. The separate, not necessarily independently structured benefit agent (and certainly not structured as defined in the invention if not added with the premix) may be other hydrophobic benefit agents (e.g., perfumes, shine enhancing benefit agents, emollients) or hydrophilic benefit agents (e.g., glycerol).

BACKGROUND

Hydrophobic benefit agents (e.g., oils) can provide moisturizing and/or conditioning benefits to the skin or to hair. At present, however, it is extremely difficult to achieve high levels of deposition of these benefit agents when delivered from personal product compositions, including but not limited to personal wash liquid cleansers and personal product bar cleansers.

While this and co-pending applications are described with skin cleansing personal product language, to the extent the structured benefit agents can be used in a variety of other compositions where deposition of benefit agents is desirable (e.g., hair, deodorant), the claims are intended to be read expansively and limited only by the structuring component.

Specifically, applicants have now unexpectedly found that use of certain "structured" benefit agents (e.g., oils and other hydrophobic benefit agents) act as so-called delivery vehicles for the benefit agent(s) which they are structuring leading to multiple benefits relative to benefit agents which are delivered without the specific structuring of the invention; or to other benefit agents used in final compositions where no other structured benefit agents are used. According to the invention, preferably the benefit agent being structured and the structuring material (e.g., crystalline wax) are separate components.

By specifically selecting particular crystalline structurant or structurants (i.e., so that the crystals have specifically defined aspect ratios), and by separately preparing structured benefit agent as a premix in the manner described (i.e., separate preparation and incorporation into product in a molten, semi-molten, or solid state), the benefit agent structurant vehicle (i.e., structured benefit agent vehicle) provides enhanced deposition as well as desired in-use and after-use sensory attributes (e.g., smooth skin feel).

As noted, such structured benefit agent also helps deposition of other benefit agents whether used in the same pre-mix (it is not clear whether they are separately structured or trapped in a network, but result is same), or whether separately added with other composition components.

Specifically, the invention relates to the use of hydrophobic benefit agent or agents structured by crystalline structurant or structurants selected from the group consisting of natural and synthetic crystalline structuring materials (e.g., waxes) wherein, when the structured benefit vehicle is separately prepared before combining with the personal product bar composition, the final composition is provided with benefit agent deposition to substrate of at least 5% greater, preferably at least 10% greater and often far more than the level of deposition obtained if the benefit agent were added without being structured or without being in the presence of a structured benefit agent in the final formulation. In one embodiment, the benefit agent is oil and structured benefit agent provides deposition greater than about $5{:}g/cm^2$ (measured in accordance with the protocol detailed in the examples). Unlike prior art references where deposition is dependent on the large size of the benefit agent droplets (e.g., >50 micrometers average droplet diameter), the deposition results of the subject invention have no requirement of large droplet size and are not dependent on size. The structured benefit agents also provide enhanced deposition of hydrophobic or hydrophilic benefit agents separately added.

Among the natural crystalline waxes which may be used as benefit agent(s) structurant are included petroleum derived waxes such as paraffins and microcrystalline waxes; as well as animal and plant (vegetable) waxes. Among the synthetic crystalline waxes which may be used are crystalline polymers such as polyethylene.

Some prior art references purport to use rheological parameters to select oils or oil blends to be used for improving deposition or providing favorable sensory feel.

U.S. Pat. No. 5,674,511 to Kacher et al., for example, describes the use of solubility parameters and four rheological parameters to select benefit agents (i.e., oil or oil blends) that can be used in moisturizing cleansing formulations to improve deposition and provide favorable sensory feels. Petrolatum and petrolatum-containing mixtures are said to be favorable selections. The reference fails to teach or suggest the building of a deformable network of crystals within the benefit agent, and which crystals must have a specific aspect ratio. The Kacher reference fails to teach or suggest that the structured benefit agent can be combined with other components in the compositions in a molten or semi-molten or solid state.

Also, it does not describe separate benefit agent and structurant, as is preferred by the subject invention (i.e., in the subject invention, if petrolatum is used, it is preferably used as a structurant to structure other benefit agents rather than itself comprise the structured benefit agent). In short, the benefit agents (e.g., oils) of Kacher clearly do not appear to be internally structured delivery vehicles like those used in the compositions of the invention which are separately prepared and wherein structurant has a defined aspect ratio.

A number of prior art references disclose generally the concept of an oil additive which can thicken or stabilize oils. They do not, however teach or disclose that specific crystalline structurant (i.e., having a defined aspect ratio), when prepared in a combination with a hydrophobic benefit agent as a premix/delivery vehicle (added in molten, semi-molten or solid state and combined with a carrying composition) will enhance deposition (by an amount of at least 5%) and/or will provide enhanced sensory benefits. Moreover, in contrast to these references where deposition is disclosed as a function of large droplet size of the benefit agent, in the subject invention deposition will occur independent of such large droplet size requirement.

U.S. Pat. No. 5,804,540 to Tsaur et al. and U.S. Pat. No. 5,661,189 to Grieveson, for example, disclose use of both crystalline or micro-crystalline waxes and hydrophobic polymers to thicken low viscosity oil so as to control the oil droplet size (i.e., it must attain a certain minimum size to deposit) as well as to maintain high lather when incorporated into a liquid cleansing composition.

U.S. Pat. No. 5,817,609 to He et al. discloses the use of hydrophobic polymers and micro-crystalline waxes to thicken low viscosity oil in bar compositions so as to achieve a large oil droplet size for deposition onto skin and to resist phase separation during bar processing.

As noted above, however, there is no discussion of the criticality of crystalline structure (aspect ratio) or that a thickened benefit agent must be separately prepared and added to the carrying composition in a molten, semi-molten or solid state. Indeed, the thickened oil is heated to 95° C. and then all of the other ingredients of the formulation are introduced into the mixer and mixed over 1-2 hours to achieve homogeneity. Further, as noted, there is no recognition that it is critical the thickener must be a natural or synthetic crystalline structuring material (as is the case with subject invention) or that deposition occurs without the need for large droplet size. Indeed, the preferred thickening materials claimed in these patents provide little to no enhancement of deposition of low viscosity oils when they are incorporated into our invention, as illustrated in the Examples Section.

In co-pending U.S. patent application Ser. No. 09/859,862 to Aronson et al. (entitled "Wet-Skin Treatment Composition"), filed May 17, 2001 and Ser. No. 09/859,849 to Aronson et al. (entitled "Method of Enhanced Moisture or Reduced Drying Using Wet-Skin Treatment Compositions"), there is disclosed benefit agents which provide a draggy feel. There is no teaching or disclosure however, of using benefit agent structurant with crystalline materials of specific aspect ratio or of how to produce such.

No prior art of which applicants are aware demonstrates the use of natural or synthetic crystalline structurants (e.g., wax) having specific aspect ratio of crystals and prepared as a premix to enhance the deposition of benefit agents (e.g., skin nutrients such as, for example, sunflower seed oil).

BRIEF DESCRIPTION OF THE INVENTION

Accordingly, the present invention relates to personal product bar compositions comprising a structured benefit agent composition for delivering a benefit agent(s) (e.g., oil) wherein said composition comprises:

(1) 1 to 80%, preferably 3 to 65% by wt. surfactant; and
(2) 0.1 to 90% by wt. of a benefit agent delivery vehicle (structured benefit agent) wherein:
  (a) 0.1 to 99%, preferably 0.5 to 99.5, more preferably 1 to 99% by wt. of the structured delivery vehicle comprises one or more benefit agents or mixtures thereof; and
  (b) 99.9 to 0.1%, preferably 99.5 to 0.5% by wt. of the structured delivery vehicle comprises a crystalline structurant or structurants selected from the group consisting of natural and synthetic materials (e.g., waxes). Among natural crystalline waxes is included petroleum derived waxes (paraffin, microcrystalline waxes), animal waxes and plant waxes. Among synthetic crystalline waxes is included crystalline polymers such as, for example, polyethylene, and synthetic derivatives of natural waxes
  wherein crystals of the crystalline structurant (e.g. wax) have an aspect or axial ratio such that length A to width B of the crystals has a ratio A/B>1, The length is to be understood as the longer of the two dimensions when considering both length and width.

When said premix (structured benefit agent composition) is separately prepared and properly combined with a carrying composition (i.e., surfactant containing personal product bar composition), in which the structured benefit agent will be used to deliver the benefit agent to the substrate, said composition will have benefit agent deposition of greater than about 5%, preferably greater than 10% relative to level of deposition from the final composition if the benefit agent had not been structured, or if the benefit agent had not been in the presence of a structured benefit agent. In one embodiment, the benefit agent is oil and deposition is greater than about $5{:}g/cm^2$, preferably at least $10{:}g/cm^2$, more preferably at least $20{:}g/cm^2$. The structured benefit agent premix can be in the form of a liquid, i.e., molten, semi-molten or solid state when added to the carrying composition which itself will generally be in molten or semi-molten state. The deposition of the benefit agent is not dependent on large droplet size (i.e., can be small or large drops).

The use of structured benefit agent also enhances delivery of benefit agent(s) in the premix which may not be independently structured (e.g., may be caught in a network) or which may be added separately and not as part of the premix.

As noted, the structured benefit agent or delivery vehicle of this invention may be used in personal product bar compositions. The composition will typically comprise (a) 1 to 80%, preferably 3 to 65% of a surfactant system comprising a surfactant or surfactants selected from the group consisting of anionic, nonionic, amphoteric/zwitterionic, cationic surfactants and mixtures thereof and (b) 0.1 to 90%, preferably 0.5 to 80%, even more preferably 1-40% by weight of the structured benefit agent delivery vehicle as defined above.

In another aspect of the invention, the invention comprises a process for forming a personal product composition comprising the delivery vehicle noted above which process comprises:

(1) mixing hydrophobic benefit agent or agents and crystalline structurant at a temperature above the melting point of the structurant and then either cooling to ambient temperature so that it can be combined later with the bar carrying composition, or optionally cooling to the temperature at which the carrying composition is mixed before combining with the carrying composition;
(2) combining said separately prepared premix and the carrying composition, preferably with stirring or mixing at elevated temperature;
and then either
(3) pouring the resulting mixture into molds and cooling (actively or passively) to room temperature;
or
(4) cooling the resulting mixture to flakes (e.g., by passing mixture over a chill roll), taking the flakes (e.g., from the chill roll) and extruding the material into a billet which may then be formed or stamped.

In another embodiment, the invention provides a method for enhancing deposition of benefit agent, and provide a smooth skin feel which method comprises applying a personal product cleanser comprising:

(a) 1 to 80%, preferably 3 to 65% by wt. surfactant; and
(b) 0.1 to 90% of benefit agent delivery vehicle wherein:

(i) 0.1 to 99.9% by wt. structured benefit agent vehicle comprises one or more benefit agents or mixtures thereof; and (ii) 99.9 to 0.1% by wt. of structured benefit agent vehicle comprises a crystalline structurant wherein the structurant is selected as noted above.

DETAILED DESCRIPTION OF THE INVENTION

The present invention relates to a personal product bar composition comprising a structured benefit agent delivery vehicle composition which, because of the structure of the crystal used to prepare it (for example, aspect ratio of the crystalline structurants), and, because of its manner of preparation (separately prepared), forms a structured benefit agent component which has particular properties (e.g., yield stress, shear thinning) which permit the structured benefit agent component to deposit more efficiently from the composition onto skin or other substrate. Further, use of the structured benefit agents, permits enhanced deposition of other benefit agents in the premix (whether entrapped or independently added) as well as those in the composition that are separately added.

Figure 1:
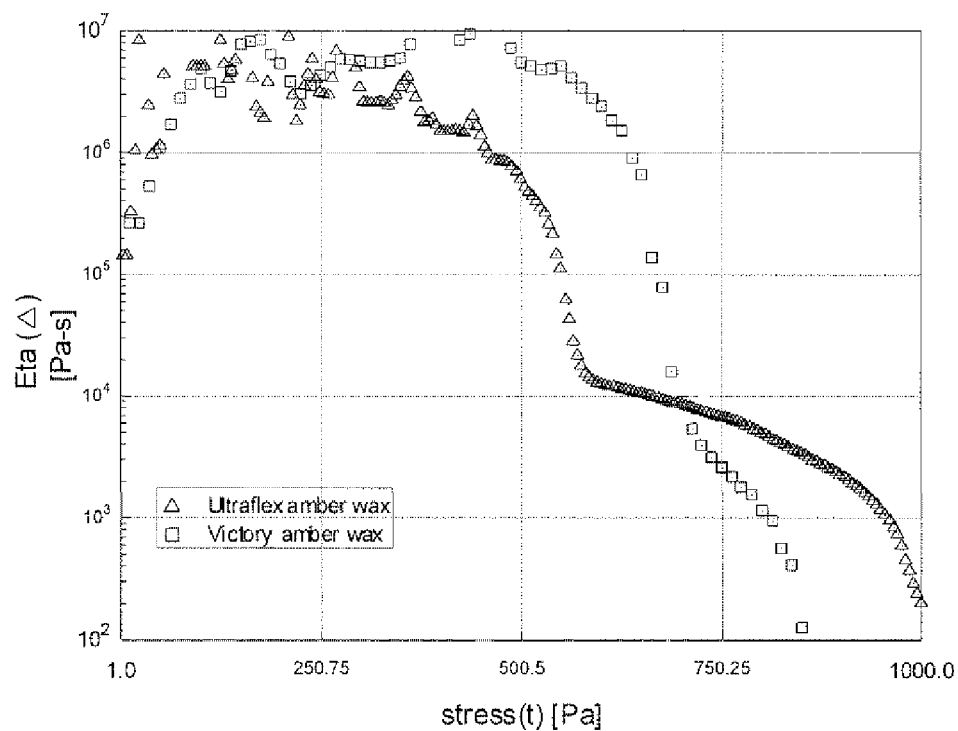
FIG. 1 is a yield stress plot of a structured benefit agent composition comprising sunflower seed oil structured with a wax (Ultraflex amber or Victory amber) of the invention. Ultraflex amber wax and Victory amber wax were each mixed with sunflower seed oil at a ratio of wax/oil of 1:4. The graph shows how the structured benefit agent yields under high stress, a property specific to the structured benefit agents of the invention. At low stresses the viscosity of the structured benefit agent composition, (measured in Pascal seconds, or Pa-s) is essentially constant. As the applied stress is increased and reaches the yield stress value, the viscosity drops sharply and the material flows more readily.
Figure 2:
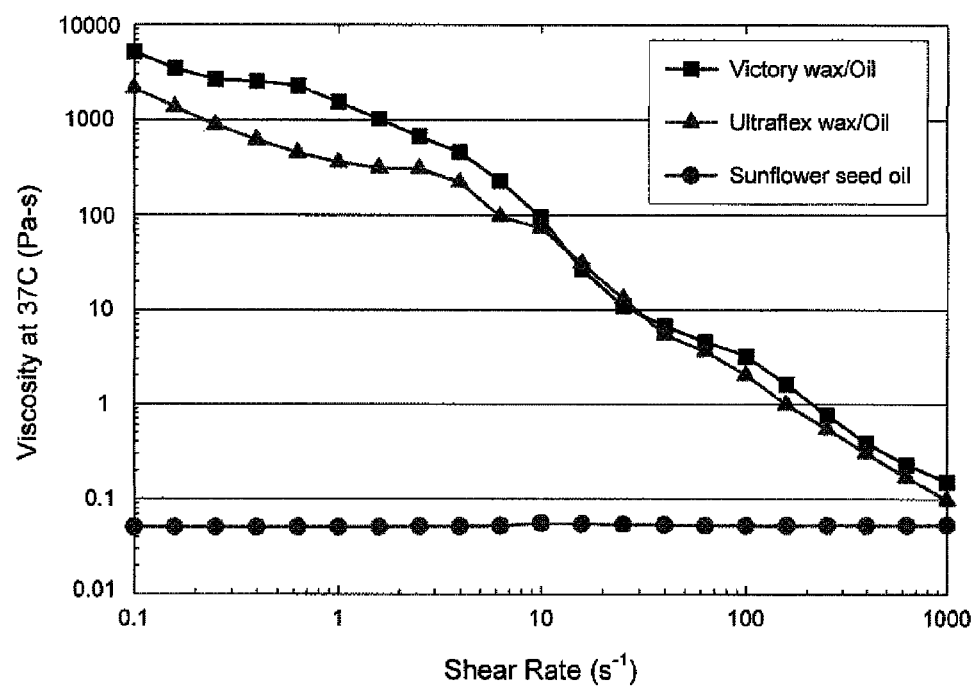
FIG. 2 is a plot showing shear thinning behavior of structured benefit agents of is the invention versus an unstructured benefit agent. Ultraflex amber wax and Victory amber wax were each mixed with sunflower seed oil at a ratio of wax/oil of 1:4. For comparison, the viscosity behavior with shear of unstructured sunflower seed oil is also shown. Plotted is viscosity versus shear rate. At low shear rates the viscosity of structured benefit agents, sunflower seed oil structured with wax (Ultraflex amber wax or Victory amber wax) is very high. As the applied shear rate is increased the viscosity of the structured benefit agents decreases and continues to decrease at the higher shear rates. At sufficiently high shear rates the viscosity of structured benefit agents approaches that of the pure unstructured benefit agent component.

Yield stress parameters can be 1-5000 Pa or higher and all ranges subsumed therein (see FIG. 1) and shear thinning parameters can range from 2000 Pa·s (or higher) at low shear rates (0.1/sec) (i.e., viscosity of 1000 to 10,000 Pa·s as seen on the Y axis of FIG. 2) to 0.1 Pa·s (or lower) at high shear rates (100/sec) (again, see FIG. 2). Both yield stress and shear-thinning parameters/ranges are dependent on the level of benefit agent structurant added to benefit agent.

When specific crystalline materials are used to structure the structured benefit agent, and when the process of the invention is used, a final composition containing the structured benefit agent vehicle will deliver hydrophobic benefit agent to the skin or substrate at an efficient level, i.e., at least 5% greater than if not used. Moreover, such deposition is not dependent on large droplet size of the structured benefit agent droplets in the carrying composition (e.g., bar soaps).

The "structured" benefit agent (e.g., oil) of the subject invention can be envisioned as an emollient droplet which has certain physical properties defining at least in part the ability of the structured benefit agent to deliver the benefit agent more efficiently from the final composition.

More specifically, when crystalline waxes structure the benefit agent, the crystals in the benefit agent phase are believed to create a solid network which is apparently interconnected like a "house of cards" for plate-like crystals or perhaps more like a scaffold structure when the crystalline structurant has rod/needle morphology. The crystals form a three-dimensional supporting network that, without wishing to be bound by theory, is believed to make the wax structured benefit agents, for example, more than just thickened benefit agents (see FIG. 4). The crystalline structure changes the normally fluid benefit agent (e.g., vegetable or other oils) into solid-like materials that have good flow and spreading properties for benefit agent deposition. Through selection of structurant (e.g., wax) and calculation of structurant content, the structured benefit agent can be tailored to meet desired rheological parameters. An important part of the invention is that the crystal forming this 3-D network must have an aspect or axial ratio of length and width (A and B, respectively) such that A/B>1. This aspect ratio of the crystals is believed to enhance deposition of the structured benefit agent (see FIG. 3).

The structured benefit agents of the invention have been found to deposit much better from the personal product bar cleansers than if the benefit agent is not structured. Again, while not wishing to be bound by theory, deposition is believed to occur by direct transfer where the affinity of the structured benefit agent for surfaces is related to the properties of the crystals (e.g., aspect ratio) used to structure.

The structured benefit agent can be seen as a premix since it is a critical aspect of the invention that the benefit agent being structured and the crystalline structurant forming the "structure" be combined before adding to the carrying composition in which the structured benefit agent will be used. In this sense, the premix or structured benefit agent is acting as a vehicle for delivery of the benefit agent. On the other hand, the structured benefit agent may also enhance deposition of other benefit agents either by entrapping these benefit agents in a network formed by the structured benefit agent (if other benefit agent is in premix for example) or even if the other benefit agent is separately added to the composition separate from the premix.

The structured benefit agent vehicle specifically comprises:

(a) 0.1 to 99.5%, preferably 0.5 to 99.5% by wt. (including all ranges subsumed therein) of the vehicle comprising one or more benefit agents or mixtures thereof; and (b) 99.9 to 0.1, preferably 99.5 to 0.5% by wt. (including all ranges subsumed therein) of the vehicle comprising a crystalline structurant selected from the group consisting of natural and synthetic crystalline materials (e.g., waxes).

Benefit Agent The benefit agent of the subject invention may be a single benefit agent component. Further the benefit agent may be a mixture of two or more components, one or all of which may have a beneficial aspect.

As noted, a separate benefit agent may also have enhanced deposition, even if it is not clear this is due to structuring or because it is entrapped in a network. Further, the structured benefit agent may enhance deposition of a benefit agent which is separately added (see, for example, applicants' copending application which is hereby incorporated by reference relating to enhanced hydrophilic benefit agent deposition).

The benefit agents can be emollients, moisturizers, anti-aging agents, anti-inflammatory agents, skin-toning agents, skin lightening agents, sun screens, fragrances, etc.

The preferred list of benefit agents include:

(a) silicone oils, gums and modifications thereof such as linear and cyclic polydimethylsiloxanes; amino, alkyl alkylaryl and aryl silicone oils, (b) fats and oils including natural fats and oils such as jojoba, soybean, sunflower seed oil, rice bran, avocado, almond, olive, sesame, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts, (e) hydrocarbons such as liquid paraffins, petrolatum, vaseline, microcrystalline wax, ceresin, squalene, pristan, paraffin wax and mineral oil;

(f) higher fatty acids such as behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) octocrylene(2-ethylhexyl 2-cyano-3,3-diphenylacrylate), octyl salicylate (2 ethylhexyl salicylate), benzophenone-3 (2-hydroxy-4-methoxy benzophenone), and avobenzone (4-tert-butyl-4'-methoxydibenzoylmethane) (these are merely illustrative);

(m) phospholipids;

(n) particles having a wide range of shapes, surface characteristics, and hardness characteristics which can be utilized to provide optical effect. The water-insoluble particles can be derived from a wide variety of materials including those derived from inorganic, organic, natural, and synthetic sources. Non-limiting examples of these materials include those selected from the group consisting of almond meal, alumina, aluminum oxide, titanium dioxide, mica, coated mica, sodium stearate, stearic acid, zinc stearate, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e., polytetrafluoroethylene), polyhalogenated olefins, pumice rice bran, rye flour, sericite, silica, silk sodium bicarbonate, sodium silicoaluminate, soy flour synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like; and (o) anti-aging, wrinkle-reducing, skin whitening, anti-acne, and sebum reduction agents such as alpha-hydroxy acids and esters, beta-hydroxy acids and ester, polyhydroxy acids and esters, kojic acid and esters, ferulic acid and ferulate derivatives, vanillic acid and esters, dioic acids (such as sebacid and azoleic acids) and esters, retinol, retinal, retinyl esters, hydroquinone, t-butyl hydroquinone, mulberry extract, licorice extract, and resorcinol derivatives;

(p) fragrance molecules which include acetanisol; amyl acetate; anisic aldehyde; anisole; anisylalcohol; benzaldehyde; benzyl acetate; benzyl acetone; benzyl alcohol; benzyl formate; hexenol; laevo-carveol; d-carvone; cinnamaldehyde; cinnamic alcohol; cinnamyl acetate; cinnamyl formate; cis-3-hexenyl acetate; Cyclal C (2,4-dimethyl-3-cyclohexen-1-carbaldehyde);

dihydroxyindole; dimethyl benzyl carbinol; ethyl acetate; ethyl acetoacetate; ethyl butanoate; ethyl butyrate; ethyl vanillin; tricyclo decenyl propionate; furfural; hexanal; hexenol; hydratropic alcohol; hydroxycitronellal; indole; isoamyl alcohol; isopulegyl acetate; isoquinoline, ligustral; linalool oxide; methyl acetophenone; methyl amyl ketone; methyl anthranilate; methyl benzoate; methyl benzyl acetate; methyl heptenone, methyl heptyl ketone; methyl phenyl carbinyl acetate; methyl salicylate; octalactone; para-cresol; para-methoxy acetophenone; para-methyl acetophenone; phenethylalcohol; phenoxy ethanol; phenyl acetaldehyde; phenyl ethyl acetate; phenyl ethyl alcohol; prenyl acetate; propyl butyrate; safrole; vanillin; viridine, allyl caproate, allyl heptoate, anisole, camphene, carvacrol, carvone, citral, citronellal, citronellol, citronellyl acetate, citronellyl nitrile, coumarin, cyclohexyl ethylacetate, p-cymene, decanal, dihydromyrcenol, dihydromyrcenyl acetate, dimethyl octano, ethyllinalool, ethylhexyl ketone, eucalyptol, fenchyl acetate, geraniol, gernyl formate, hexenyl isobutyrate, hexyl acetate, hexyl neopentanoate, heptanal, isobornyl acetate, isoeugenol, isomenthone, isononyl acetate, isononyl alcohol, isomenthol, isopulegol, limonene, linalool, linalyl acetate, menthyl acetate, methyl chavicol, methyl octyl acetaldehyde, myrcene, napthalene, nerol, neral, nonanal, 2-nonanone, nonyl acetate, octanol, octanal, α-pinene, β-pinene, rose oxide, α-terpinene, γ-terpinene, α-terpinenol, terpinolene, terpinyl acetate, tetrahydrolinalool, tetrahydromyrcenol, undecenal, veratrol, verdox, allyl cyclohexane propionate, ambrettolide, Ambrox DL (dodecahydro-3a,6,6,9a-tetramethyl-naphtho[2,1-b]furan), amyl benzoate, amyl cinnamate, amyl cinnamic aldehyde, amyl salicylate, anethol, aurantiol, benzophenone, benzyl butyrate, benzyl iso-valerate, benzyl salicylate, cadinene, campylcyclohexal, cedrol, cedryl acetate, cinnamyl cinnamate, citronellyl isobutyrate, citronellyl propionate, cuminic aldehyde, cyclohexylsalicylate, cyclamen aldehyde, dihydro isojamonate, diphenyl methane, diphenyl oxide, dodecanal, dodecalactone, ethylene brassylate, ethylmethyl phenylglycidate, ethyl undecylenate, exaltolide, Galoxilide™ (1,3,4,6,7,8-hexhydro,4,6,6,7,8,8-hexamethyl-cyclopenta-γ-2-benzopyran), geranyl acetate, geranyl isobutyrate, hexadecanolide, hexenyl salicylate, hexyl cinnamic aldehyde, hexyl salicylate, α-ionone, β-ionone, (-ionone, α-irone, isobutyl benzoate, isobutyl quinoline, Iso E Super™ (7-acettl,1,2,3,4,5,6,7,8-octahydro,1,1,6,7-tetramethyl napthalene), cis-jasmone, lilial, linalyl benzoate, 20methoxy naphthaline, methyl cinnamate, methyl eugenol, (-methylionone, methyl linolate, methyl linolenate, musk indanone, musk ketone, musk tibetine, myristicin, neryl acetate, δ-nonalactone, (-nonalactone, patchouli alcohol, phantolide, phenylethyl benzoate, phenylethylphenylacetate, phenyl heptanol, phenyl hexanol, α-santalol, thibetolide, tonalid, δ-undecalactone, (-undecalactone, vertenex, vetiveryl acetate, yara-yara, ylangene; and (q) mixtures of any of the foregoing benefit agents.

To the extent materials above are hydrophobic, they are delivered as part of the premix (and made probably, although not necessarily are structured; that is, at least one hydrophobic benefit agent will be structured, but others may be entrapped in the benefit agent network). Although not listed above, hydrophilic benefit agents may also be entrapped in the structured benefit agent network of the premix or separately added outside the premix. This is discussed, for example, in applicants' copending application relating to hydrophilic benefit agents hereby incorporated by reference into the subject application.

Natural or Synthetic Crystalline Structurant

The crystalline structurant used for "structuring" the benefit agent oil or emollient of the subject invention may be a natural or synthetic crystalline wax. Mineral, animal or plant (vegetable) waxes are all described as natural waxes. Synthetic waxes are described as those waxes that have been synthetically polymerized from raw materials or chemically modified natural waxes.

Among the natural crystalline waxes which may be used are petroleum based waxes such as paraffins and microcrystalline wax. Chemically, both microcrystalline (MC) and paraffin waxes are very similar, consisting of long saturated hydrocarbon chains. Both types of waxes are separated from crude petroleum with the MC waxes typically having higher molecular weights. Paraffin wax is extracted from the high boiling fractions of crude petroleum during the refining process by cooling and filtering. Following a sweating process to remove remaining oil in the wax, the resulting paraffin wax typically has less than 0.5% oil. There are many different grades available mostly varying in melting point. Generally, paraffin waxes are colorless or white and transparent. Paraffin waxes consist mainly of straight chain molecules with a small amount of branched-chain molecules mostly having branching near the end of the chains. As a result of the long, straight chains, paraffin wax has large, well-formed crystals. Molecular weights of paraffin waxes generally range from 360 to 420 (26 to 30 carbon atoms), although versions with longer chains (molecular weights up to 600) are available. Typical melting points are 126-134° F. (52-57° C.), the high molecular weight versions have melting points near 170° F. (77° C.). Paraffin waxes are brittle and the addition of oil weakens the structure (lowers the tensile strength).

Microcrystalline waxes (MC) differ from paraffin waxes in physical properties, chain structure and length, and in the process of manufacture. They are tougher, more flexible and have higher tensile strength and melting points than paraffin waxes. MC waxes have high affinity for oil which, when added, increases the wax plasticity. MC wax cannot be distilled without decomposition and therefore is separated from the residual distillation fraction of crude petroleum by dewaxing processes involving recrystallization in organic solvents and centrifugation. Oil content varies with grade but is usually around 2 to 12%. MC waxes contain mostly branched-chain molecules located at random along the chain with some straight chains. Typical melting points are 145 to 195° F. (63-91° C.). A high penetration number indicates flexibility of the wax, but flexibility is not a function of melting point.

There are also other mineral waxes such as montan wax, lignite wax, osocerite, ceresin, utah wax and peat wax.

Animal waxes can be obtained from such things as bees, insects or whales, These waxes include but are not limited to beeswax, Chinese wax, shellac wax, spermaceti and wool wax. Beeswax, for example, classified as an animal wax, is secreted by the honey bee to construct the honeycomb. The wax is harvested by melting the honeycomb and filtering away the wax. Beeswax has melting points around 61-65° C. and is compatible with almost all waxes and oils.

Plant waxes can be derived from beans, leaves and berries. Plant or vegetable waxes can include bayberry, candelilla, carnauba, cotton, esparto, fir, Japan, ouricury, palm, rice-oil, sugar cane, ucuhuba and cocoa butter.

Among synthetic crystalline waxes which may be used are crystalline polymers such as polyethylene, polymethylene (including those synthesized by Fischer-Tropsch methodology), chemically modified waxes, polymerized alpha olefins and synthetic animal waxes. For example, siliconyl beeswax may be used which is beeswax that has been chemically modified.

A sample of various waxes which may be used according to the subject invention and of their properties is set forth below in Table 1.

TABLE 1

Waxes and their Properties

| Wax | Manufacturer | Classification* | Penetration No.** (25° C.) | Melting Point (° C.) |
|---|---|---|---|---|
| Ultraflex Amber | Bareco Products | MC | 27 | 74.1 |
| Victory Amber | Bareco Products | MC | 28 | 79.1 |
| White Petrolatum | Penreco | MC | — | 54 |
| Multiwax ML-445 | Crompton Corp. | MC | 30 | 79.4 |
| Multiwax 180-M | Crompton Corp. | MC | 18 | 85 |
| Multiwax W-835 | Crompton Corp. | MC | 70 | 76.7 |
| Multiwax X145A | Crompton Corp. | MC | 40 | 74 |
| Paraffin Wax 50/155 | Frank B. Ross Co., Inc. | P | 12 | 67 |
| Siliconyl Beeswax | Koster Kuenen, Inc. | DN | N/A | 70 |
| Be Square 175 white | Bareco Products | MC | 15 | 82.5 |
| Be Square 175 black | Bareco Products | MC | 18 | 82.3 |
| Perrowax 2250F | The International Group | MC | N/A | 40 |
| Beeswax NF | Frank B. Ross Co., Inc. | N | 18 | 62.5 |

*MC: microcrystalline;
P: paraffin;
N: natural/animal;
dN: derivative of natural/animal wax
**Penetration No.: Penetration number values as reported by manufacturers using the standard test method for needle penetration of petroleum waxes of the American Society for Testing and Materials (ASTM D1321). The depth of penetration of needle in tenths of a millimeter (dmm) is measured with a penetrometer that applies a standard needle to the sample for 5 seconds under a load of 100 grams.

Another structuring material of the invention (e.g., used for structuring other benefit agents) is the microcrystalline wax petrolatum (also known as petrolatum or mineral jelly), which typically comprises about 90% by wt. of a natural mixture of microcrystalline waxes plus minor amounts of other impurities.

Structured Benefit Agent

As noted above, the wax in the benefit agent is believed to form a three-dimensional supporting network which is believed to make the structured benefit agent more than just thickened benefit agents. That is, it changes the consistency of the fluid benefit agent (e.g., oil) to a solid-like material having good spreading/deposition properties. Deposition is believed to occur by transfer of structured benefit agent droplets/particles to the substrate surface from the composition where the crystalline structure of the structuring material crystals (e.g., aspect ratio) is believed to help enhance affinity of the structured benefit agent to the substrate.

Other benefit agents in the premix may also structure (i.e., 2 or more) or just one may structure and/or the other benefit agent may have enhanced deposition by being entrapped in the network formed by the structured benefit agent.

The benefit agent may comprise 0.1 to 99.9% by wt. of the delivery vehicle/premix and structurant may comprise 99.9 to 1% by wt. of the delivery vehicle. Preferably benefit agent is 0.5 to 99.5%, more preferably 1 to 99% of vehicle. In some preferred embodiment, benefit agent comprises 50-99% of vehicle while wax is 1 to 50%, preferably 2 to 45% of benefit agent vehicle.

When used, for example, as part of a bar composition where structuring material (e.g., wax) is 20% of the benefit agent phase, structured benefit agent may exist as separate domain, whose size may be, for example, in the range of 1-50:m (or potentially even much larger). As noted, however, there is no requirement that these domains or droplets be of any particular size. The droplets may be somewhat spherical but have a rough, textured surface, a result of the structurant crystal within the drops.

As mentioned, there is no large size requirement for the structured benefit agent domains or droplets of the invention. Unlike prior art, the structured benefit agent can deposit high benefit agent amounts even at small droplet sizes, i.e., below 10:m and possibly even submicron.

As also mentioned, low levels (<50% of structured benefit agent) of structurant can be used.

Figure 3:
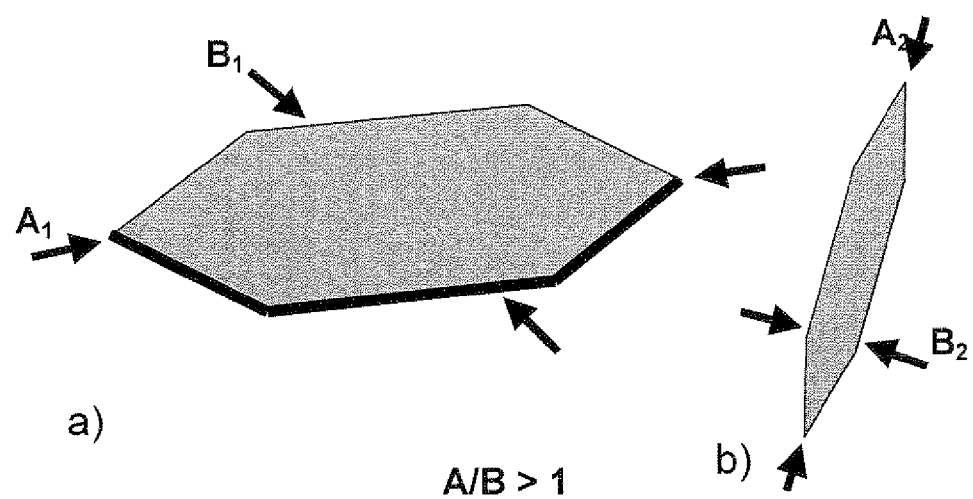
FIGS. 3a and 3b are schematics of typical crystal structurants of the invention having length "A" and width "B". As noted, the aspect or axial ratio of A/B must be greater than 1. The length is to be understood as the longer of the two dimensions when considering length and width.
Figure 4:
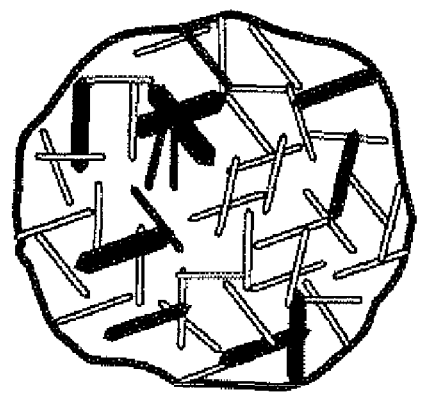
FIG. 4 is a schematic of structurant crystals (which can be "plate-like") forming a three-dimensional network within the structured benefit agent (e.g., oil).

The only criticality is that the shape of the structurant have high axial or aspect ratio (A/B>1). This is shown in FIG. 3. The length is to be understood as the longer of the two dimensions when considering length and width. The fact that structuring exists is shown by high yield stress observed on benefit agents even when using low amount of structurant (see FIG. 1).

The structured benefit agent of the invention may also be used in combination with other materials that have been shown to enhance the deposition of hydrophobic benefit agents (e.g., cationic polymers, inorganic thickening agents such as clays or silicas, and polymer thickening agents).

Finally, as noted, the structured benefit agent may enhance deposition of other non-structured benefit agents which are not part of the premix. This phenomenon is described, for example in one of applicants co-filed, co-pending applications.

Process

A critical aspect of the subject invention is that the benefit agent and crystalline structurant must be intimately combined (e.g., in a premix) before they are combined with the carrying composition. The combination of such premix with carrying composition can be when the structured benefit agent is in a molten, semi-molten or solid state such that it can be added to the carrying composition.

In one embodiment of the invention, the crystalline structurant and benefit agent (e.g., an emollient oil such as sunflower seed oil) are combined and may be heated to a temperature above the melting point of the structurant. These are then preferably mixed to uniformity.

The mixture can then be optionally cooled so that the structured delivery vehicle is combined with the bar carrying composition at a temperature that is appropriate to achieve proper mixing with the carrying composition for the selected bar manufacturing route (e.g., extrusion, melt cast etc.).

When such process is followed, the resulting structured benefit agent compositions will have the properties described above (i.e. shear thinning, yield stress etc.) and provide deposition of benefit agent, when measured from the carrying composition, of greater than 5%, preferably greater than 10% relative to level of deposition of benefit agent to substrate from final composition if the benefit agent had not been structured, or the benefit agent not being in the presence, in the final formulation, of a structured benefit agent. In one embodiment, the benefit agent is oil and deposition is at least about $5:g/cm^2$, preferably at least about $10:g/cm^2$, more preferably at least about $20:g/cm^2$.

Bar Compositions

In one embodiment of the invention, the premix comprising benefit agent may be used in a bar (e.g., personal cleansing bar) composition. Typically, such composition comprises as follows:

(1) 1% to 80%, preferably 3 to 65% by wt., of a surfactant selected from the group consisting of anionic, amphoteric, nonionic and cationic surfactant and mixtures thereof;

(2) 0.1% to 90%, preferably 0.5% to 80% of a delivery vehicle comprising 0.1 to 99.9% delivery vehicle benefit agent or agents and 99.9 to 0.1% delivery vehicle crystalline structurant(s) selected from the group consisting of natural and synthetic crystalline waxes;

(3) 0.1% to 80%, preferably 5% to 70% by wt. total composition of a structuring aid and/or filler;

(4) optional ingredients for personal cleansing bar; and wherein the premix (structured benefit agent) is incorporated into bar compositions as a separate premix; and wherein deposition of oil/emollient from the bar composition onto substrate is greater than about 5% greater than if the benefit agent were not structured or not in the presence of a structured benefit agent.

Surfactant System

Anionic Surfactants

The anionic surfactant may be, for example, an aliphatic sulfonate, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

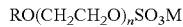
$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula

$$R^4CONHCH_2CH_2O_2CCH_2CH(SO_3M)CO_2M$$

wherein $R^4$ ranges from $C_8$-$C_{22}$ alkyl and M is a solubilizing cation;

amido-MIPA sulfosuccinates of formula

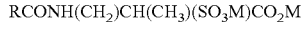
$$RCONH(CH_2)CH(CH_3)(SO_3M)CO_2M$$

where M is as defined above.

Also included are the alkoxylated citrate sulfosuccinates; andalkoxylated sulfosuccinates such as the following

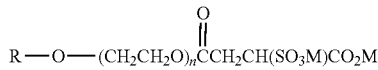

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

Another class of anionics are carboxylates such as follows:

$$R—(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5-15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application.

Another surfactant which may be used are $C_8$ to $C_{22}$ neutralized fatty acids (soap). Preferably, the soap used are straight chain, saturated $C_{12}$ to $C_{18}$ neutralized fatty acids.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

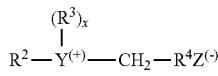

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

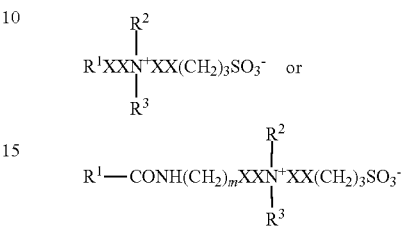

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric detergents within the above general formula include simple betaines of formula:

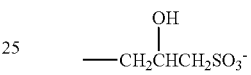

and amido betaines of formula:

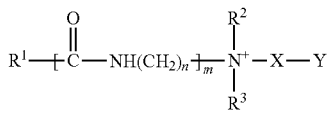

where m is 2 or 3,

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

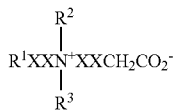

where m is 2 or 3, or variants of these in which —$(CH_2)_3$ $SO^-_3$ is replaced by

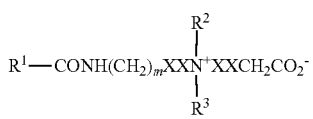

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Lienado, both of which are also incorporated into the subject application by reference.

Preferred alkyl polysaccharides are alkylpolyglycosides of the formula

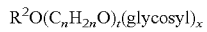

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Structurant Benefit Agent Premix

The benefit agent portion of the structured benefit agent may be any of the benefit agents described previously in the section relating to the benefit agent.

Similarly, the crystalline structurant may be any one of the materials described above.

The premix/delivery vehicle is also as described above.

As indicated earlier, the premix should be made separately and it can be in a liquid (molten), semi-molten or solid state before adding to the final carrying composition (e.g., bar composition)

When used in the composition, the structured benefit agent will permit benefit agent deposition of greater than about 5% greater than if the benefit agent had not been structured. In one embodiment, benefit agent is oil and deposition is greater than $5{:}g/cm^2$, preferably greater than $10{:}g/cm^2{}_1$ more preferably greater than $20{:}g/cm^2$ and this deposition is not dependent on large droplet size of the structured benefit agent.

Structuring Aids or Fillers

The compositions may also contain 0.1 to 80% by wt., preferably 5 to 70% by wt. of a structurant and/or filler. Such structurants can be used to enhance the bar integrity, improve the processing properties, and enhance desired user sensory profiles.

The structurant is generally long chain, preferably straight and saturated, ($C_8$-$C_{24}$) fatty acid or salt thereof or ester derivative thereof, and/or branched long chain, preferably straight and saturated, ($C_8$-$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

12-Hydroxy stearic acid may be used as a component of the bar structuring system. Such structurant is described, for example in U.S. Pat. No. 6,458,751 to Abbas et al., hereby incorporated by reference into the subject application.

Other Bar Ingredients

In addition, the bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin to (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers which may be used include Quatrisoft LM-200 Polyquaternium-24, Merquat Plus 3330-Polyquaternium 39; and Jaguar® type cationics.

Polyethylene glycols as conditioners which may be used include:

| Polyox | WSR-205 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

Cationic polymers, like other benefit agents, may be included in the bar surfactant/structurant filler carrying composition or they may be added into the premix benefit delivery vehicle along with the wax.

Typically, bars will also comprise 1 to 30%, preferably 2 to 20% water. The amount of water may vary depending on type of process and bar structuring materials used.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Preparation of Wax-Structured Benefit Agent.

Structured (e.g., wax structured) benefit agent premixes (delivery vehicles) were prepared at temperatures at or just above the melting points of the wax structurant or other mixtures of benefit agent and structuring component. Typically, the structuring material was weighed into a 100 ml stainless steel beaker and then the appropriate amount of benefit agent (e.g., sunflower seed oil) was added based on the formulation specifications. The components were then heated by placing the beaker in a thermally-controlled water bath to melt the structuring material (e.g., wax). The molten structured oil was stirred with a stainless steel spatula until uniformly mixed and maintained at the elevated temperature until use (usually no more than 5 min).

Preparation of Bar Prototypes.

Bars produced via a melt cast process route were made in Pyrex mixing vessels heated with electric heating mantles. Multiple turbine blades controlled with adjustable speed electric motors provided agitation for the vessel. Formulations were manually poured into polypropylene molds for cooling and solidification.

The base bar compositions were prepared by melting the bar structuring aids followed by addition of surfactants and then any additional components of the base formulation as required.

Bars produced via an extrusion process were mixed in a Patterson sigma blade mixer. The base bar compositions were prepared by mixing components in the order described for the cast-melt process above. The compositions were then passed over a chill roll set at 15° C. The flakes from the chill roll were then extruded through a Weber Seelander laboratory scale plodder. Bars were stamped on a Sigma Engineering air-driven press.

Sunflower Seed Oil Deposition Protocol

Full thickness porcine skin was obtained from Sinclair Research Center, Inc. It was cut into pieces of size 8 cm×10 cm. The skin was shaved with a disposable razor, rinsed with warm water and then rinsed with ethyl alcohol (10 ml) and wiped dry with an absorbent paper towel. After cleaning in this manner, the skin was then hydrated for 10 seconds under running tap water set to 100° F. The amount of bar product applied to the skin was 3.3 mg/cm$^2$. Thus, the appropriate amount of bar material was weighed out according to the area of skin to be washed and then an equal amount of water was added to the bar sample and this was then allowed to sit for 15 min at ambient temperature in a covered vessel. The slurry so formed was then transferred onto the piece of skin to be washed and spread evenly over the entire surface using one hand covered with a textured latex glove. The skin was then washed over its entire area using the gloved hand, rubbing in a circular motion for about 30 seconds. The skin was then rinsed under a tap for 10 seconds at a flow rate of 70 ml/minute and temperature of 100° F. Excess water was removed by patting the skin with a paper towel. The skin was then allowed to air dry at ambient temperature for 15 minutes. The sunflower seed oil that was deposited on the skin during the wash procedure was recovered by solvent extraction. A glass cylinder (7 cm$^2$ area) was firmly placed onto the skin surface and 2 ml of solvent (25:75 (v/v) chloroform:methanol) dispensed into the cylinder and stirred with a glass rod for 1 minute. The solvent was then transferred to a 10 ml vial using a disposable plastic pipette. The extraction process was repeated two more times and all three portions of the solvent were combined in the single vial. The sample was then filtered using a disposable syringe fitted with a 0.45 μm Millipore disposable filter. The solvent was evaporated under nitrogen. Sunflower Seed Oil Deposition Analysis by High Performance Liquid Chromatography (HPLC).

Quantification of the sunflower seed oil recovered from the skin was via high performance liquid chromatography. Following evaporation of the solvent under nitrogen as described above, the sample was reconstituted in mobile phase solvent (70:30 (v/v) acetone:acetonitrile). LC separation was performed on a Hewlett-Packard Series 1100 HPLC. Detection was via a light-scattering detector, Alltech ELSD 2000. The column used for LC separation was a Waters Symmetry $C_{18}$ (39×150 mm) kept at 30° C. The mobile phase was 70:30 (v/v) acetone:acetonitrile. The flow rate was 0.8 ml/min. The sample injection volume was 100 μl. Run time was 18 min. Detector nitrogen flow rate was 0.9 L/min and evaporative tube temperature was 40° C. (with impactor OFF). The elution time for the peak of interest was about 6.2 min.

Standards were prepared at concentrations ranging from 10 to 40 ppm of sunflower seed oil. The level of sunflower oil in the extracts was calculated based on the standard curve generated from the standard solutions.

Examples 1 and 2 and Comparatives A and B

Enhanced deposition of sunflower seed oil by structuring with a microcrystalline wax.

Bar formulations were prepared having various compositions via a melt-cast process. A composition (comparative A) was prepared by mixing 20% w/w of sunflower seed oil into a base formulation at 80° C. for 10 min. The mixture was then cooled to room temperature. A composition (comparative B) was similarly prepared by mixing 30% w/w of sunflower seed oil into a base formulation.

Comparative Formulations A and B are Set Forth Below:

| Component | Comparative A % wt | Comparative B % wt |
|---|---|---|
| Sodium cocoyl isethionate (SCI) | 20.0 | 20.0 |
| Cocoamidopropyl betaine | 5.0 | 5.0 |
| Sunflower seed oil | 20.0 | 30.0 |
| Palmitic-Stearic Acid | 16.0 | 16.0 |
| Sodium Stearate | 8.0 | 8.0 |
| Propylene Glycol | 5.0 | 5.0 |
| Glycerine | 10.0 | — |
| 82/18 tallow/coco soap | 2.8 | 2.8 |
| Water | 6.0 | 6.0 |
| Misc (e.g. Sodium Isethionate; Coconut fatty acid; Perfume; Titanium Dioxide; EDTA; EDHP; sodium chloride) | 7.2 | 7.2 |

Example 1 was prepared by mixing 20% w/w of a structured oil (comprising 4% w/w of the Victory Amber Wax structurant) into a base formulation at 80° C. for 10 min. The mixture was then cooled to room temperature. Example 2 was similarly prepared by mixing 30% w/w of a structured oil (comprising 6.0% w/w of the Victory Amber Wax structurant) into a base formulation at 80° C. for 10 min followed by cooling to room temperature. For these formulations, the structured oil was prepared by addition of the structurant to the sunflower seed oil, heating the mixture to a temperature above the melting point of the structurant and mixing until uniform. The molten structured oil was only then combined with (i.e. added to) the molten surfactant base formulation which was maintained at the same temperature as the structured oil. After mixing for 10-15 minutes, the formulation was poured into a mold and cooled to room temperature. The structurant must be, and was, added to the oil phase prior to dispersion of the structured oil phase into the molten surfactant base formulation.

These compositions of the invention are set forth below as Examples 1 and 2.

| Component | Example 1 % wt. | Example 2 % wt. |
|---|---|---|
| Sodium cocoyl isethionate | 20.0 | 20.0 |
| Cocoamidopropyl betaine | 5.0 | 5.0 |
| Sunflower seed oil | 16.0 | 24.0 |
| Victory Amber Wax | 4.0 | 6.0 |
| Palmitic-Stearic Acid | 16.0 | 16.0 |
| Sodium Stearate | 8.0 | 8.0 |
| Propylene Glycol | 5.0 | 5.0 |
| Glycerine | 10.0 | — |
| 82/18 tallow/coco soap | 2.8 | 2.8 |
| Water | 6.0 | 6.0 |
| Miscellaneous | 7.2 | 7.2 |

Table 1 below sets forth the deposition results for each of the compositions.

TABLE 1

Sunflower Seed Oil Deposition from Examples 1 and 2 and from Comparative A and B.

| Formulation | Deposition, μg/cm² |
|---|---|
| Comparative A (20% oil, no structurant) | 3 |
| Example 1 | 14 |
| Comparative B (30% oil, no structurant) | 5 |
| Example 2 | 26 |

As can be seen clearly from Table 1, deposition of sunflower seed oil is significantly enhanced when it is structured with a microcrystalline wax as in the Examples 1 and 2.

Example 3 and Comparative C

Deposition of oil is increased when the oil is structured prior to combining with the surfactant base formulation.

Example 3 was prepared via a melt cast process by mixing 25% w/w of a structured oil (comprising 5% w/w of the Victory Amber Wax structurant) into a base formulation at 75° C. for 10 min, and then cooling to room temperature. For this formulation, the structured oil was prepared by addition of the structurant to the sunflower seed oil, heating the mixture to a temperature above the melting point of the structurant and mixing until uniform. The molten structured oil was only then combined with (i.e. added to) the molten surfactant base formulation which was maintained at the same temperature as the structured oil. After mixing for 10 min, the formulation was poured into a mold and cooled to room temperature. The structurant must be, and was, added to the oil phase prior to dispersion of the structured oil phase into the molten surfactant base formulation.

Comparative C was similarly prepared by mixing 20% w/w of sunflower seed oil and 5% w/w of the Victory Amber Wax structurant into a base formulation at 75° C. for 10 min followed by cooling to room temperature. In this case, the oil and the wax structurant were not separately combined prior to combining with the molten surfactant base formulation. The compositions of Example 3 of the invention and Comparative C are set forth below:

| Component | Example 3 % wt | Comparative C % wt |
|---|---|---|
| Sodium cocoyl isethionate | 25.0 | 25.2 |
| Mackam 1 L | 15.0 | 15.1 |

-continued

| Component | Example 3 % wt | Comparative C % wt |
|---|---|---|
| Cocoamidopropyl betaine | 5.0 | 5.0 |
| Sunflower seed oil | 20.0 | 20.1 |
| Victory Amber Wax | 5.0 | 5.0 |
| Palmitic-Stearic Acid | 7.0 | 7.1 |
| Propylene Glycol | 5.0 | 5.0 |
| 12-Hydroxy stearic acid | 10.0 | 10.1 |
| Water | 4.0 | 4.0 |
| Miscellaneous | 4.0 | 2.5 |

Table 2 below sets forth the deposition results for each of the compositions.

TABLE 2

Sunflower Seed Oil Deposition from Example 3 and Comparative C.

| Formulation | Deposition, μg/cm² |
|---|---|
| Example 3 (pre-mixing of oil and oil structurant) | 50 |
| Comparative C (separate addition of oil and oil structurant) | 2 |

It can clearly be seen that the deposition of sunflower seed oil is significantly enhanced when the oil is structured with the microcrystalline wax structurant prior to its incorporation in the surfactant base formulation. When the oil and microcrystalline wax structurant are added separately to the surfactant base formulation there is no enhancement of oil deposition over that which would be obtained for an unstructured oil.

Comparative D, E and F

Structuring sunflower seed oil via a microcrystalline network is more effective in enhancing oil deposition than simple thickening of the oil.

Thickened oils disclosed in He et al. were incorporated into a base formulation and bars were produced via a melt-cast process as described in U.S. Pat. No. 5,817,609. Specifically, 20% w/w of thickened oil (a 1:1 mixture of sunflower seed oil and petrolatum in Comparative D, and a 1:1 mixture of sunflower seed oil and Geahlene® in Comparative E) was incorporated into a common base formulation. In both cases, the molten thickened oil was combined with the molten base formulation and mixed until homogeneous. The formulations were than poured into a mold and cooled to room temperature.

These compositions are set forth below as Comparative formulations D and E.

Comparative formulation F was prepared by mixing 20% w/w of sunflower seed oil into a base formulation at 80° C., for 10 min, pouring the molten mixture into a mold and cooled to room temperature.

| Component | Comparative D % wt | Comparative E % wt | Comparative F % wt |
|---|---|---|---|
| Sodium cocoyl isethionate | 20.0 | 20.0 | 20.0 |
| Cocoamidopropyl betaine | 5.0 | 5.0 | 5.0 |
| Sunflower seed oil | 10.0 | 10.0 | 20.0 |
| Petrolatum | 10.0 | — | — |
| Geahlene | — | 10.0 | — |
| Palmitic-Stearic Acid | 16.0 | 16.0 | 16.0 |
| Sodium stearate | 8.0 | 8.0 | 8.0 |
| Propylene glycol | 5.0 | 5.0 | 5.0 |
| Glycerine | 10.0 | 10 | 10 |
| 82/18 tallow/coco soap | 2.8 | 2.8 | 2.8 |
| Water | 6.0 | 6.0 | 6.0 |
| Miscellaneous | 7.2 | 7.2 | 7.2 |

Table 3 below sets forth the deposition results for the Comparative compositions D, E, F and Example 1.

TABLE 3

Sunflower Seed Oil Deposition from Comparative formulations D, E, F and Example 1.

| Formulation | Deposition, μg/cm² |
|---|---|
| Comparative D (20% thickened oil - petrolatum) | 5 |
| Comparative E (20% thickened oil - Geahlene) | 3 |
| Comparative F (20% oil, no structurant/thickener) | 6 |
| Example 1 (20% oil structured with Victory Amber Wax) | 14 |

The data in Table 3 shows that the sunflower seed oil thickened with petrolatum or with Geahlene (as disclosed in He et al.) does not deposit significantly more oil than the formulation in which sunflower seed oil was incorporated without any thickening or structuring agent, and significantly less oil than is deposited when the oil is structured with a microcrystalline wax prepared in accordance with the subject invention.

Examples 4-7 and Comparative G

Structured oils incorporated into an extruded bar formulation provide enhanced deposition of oil onto skin.

Bar formulations were prepared via an extrusion process, incorporating 15% and 20% w/w of structured oil. The compositions of Examples 4-7 were prepared by mixing the appropriate amount of structured sunflower seed oil (at ca. 70° C.) into a base formulation for 5 min in a Patterson mixer at 77° C. Once the structured oil was completely dispersed, the batch was removed from the mixer and passed over a chill roll set at 15° C. The flakes from the chill roll were then extruded through a 7.5 cm Weber Seelander laboratory scale plodder. Bars were stamped on a Sigma Engineering air-driven press.

Example 4 was prepared by mixing 15% w/w of a structured oil (comprising 3% w/w of the Victory Amber Wax structurant) into a base formulation. Example 5 was prepared by mixing 15% w/w of a structured oil (comprising 6% w/w of the Victory Amber Wax structurant) into a base formulation. Example 6 was prepared by mixing 20% w/w of a structured oil (comprising 4% w/w of the Victory Amber Wax structurant) into a base formulation. Example 7 was prepared by mixing 20% w/w of a structured oil (comprising 8% w/w of the Victory Amber Wax structurant) into a base formulation. For these formulations, the structured oil was prepared by addition of the structurant to the sunflower seed oil, heating the mixture to a temperature above the melting point of the structurant and mixing until uniform. The molten structured oil was only then combined with (i.e. added to) the surfactant base formulation which was maintained at a temperature close to that of the structured oil. The structurant must be, and was, added to the oil phase prior to dispersion of the structured oil phase into the surfactant base formulation.

A composition (Comparative G) was similarly prepared by mixing 20% w/w of sunflower seed oil into a base formulation.

The formulations of Examples 4-7 and Comparative G are set forth below:

| Component | Example 4 % wt | Example 5 % wt | Example 6 % wt | Example 7 % wt | Comparative G % wt |
|---|---|---|---|---|---|
| Sodium cocoyl isethionate | 21.25 | 21.25 | 20.0 | 20.0 | 20.0 |
| Cocoamido propyl betaine | 4.25 | 4.25 | 4.0 | 4.0 | 4.0 |
| Sunflower seed oil | 12.0 | 9.0 | 16.0 | 12.0 | 20.0 |
| Victory Amber Wax | 3.0 | 6.0 | 4.0 | 8.0 | — |
| Sodium Isethionate | 4.25 | 4.25 | 4.0 | 4.0 | 4.0 |
| Palmitic-Stearic Acid | 20.0 | 20.0 | 18.9 | 18.9 | 18.9 |
| Sodium stearate | 12.0 | 12.0 | 11.4 | 11.4 | 11.4 |
| Coconut Fatty Acid | 1.35 | 1.35 | 1.20 | 1.20 | 1.20 |
| Polyethylene Glycol (MW 8000) | 12.6 | 12.6 | 11.8 | 11.8 | 11.8 |
| Polyethylene Glycol (MW 1450) | 2.2 | 2.2 | 2.0 | 2.0 | 2.0 |
| Polyethylene Glycol (MW 300) | 1.5 | 1.5 | 1.4 | 1.4 | 1.4 |
| Water | 4.1 | 4.1 | 3.9 | 3.9 | 3.9 |
| Miscellaneous | 1.5 | 1.5 | 1.4 | 1.4 | 1.4 |

TABLE 4

Sunflower Seed Oil Deposition from Examples
4-7 and from Comparative Formulation G.

| Formulation | Deposition, $\mu g/cm^2$ |
|---|---|
| Example 4 (15% structured oil; 3% structurant) | 10 |
| Example 5 (15% structured oil; 6% structurant) | 8 |
| Example 6 (20% structured oil; 4% structurant) | 14 |
| Example 7 (20% structured oil; 8% structurant) | 15 |
| Comparative G (20% oil; no structurant) | 5 |

As can clearly be seen, the structured oil compositions of the invention deposit significantly higher levels of oil than the bar formulation wherein the oil is incorporated without the structuring agent of the invention.

The invention claimed is:

1. A process for forming a personal product bar composition comprising:
   (1) 1% to 80% of a surfactant selected from the group consisting of anionic, nonionic, amphoteric, cationic surfactants and mixtures thereof; and
   (2) a structured benefit agent delivery vehicle composition consisting essentially of:
      (a) 0.1 to 99.9% by wt. of structured benefit agent composition comprising one or more hydrophobic benefit agents or mixtures thereof; and
      (b) 99.9 to 0.1% structuring material wherein said structuring material is selected from the group consisting of paraffin, victory amber wax and mixtures thereof;
   (3) 0.1 to 80% structuring aid and/or filler,
   wherein, when said structured benefit agent is separately formed and separately combined with or to a carrying composition in which the structured benefit agent will be used to deliver benefit agent onto skin, there will be provided at least a 5% increase in deposition of benefit agent to the skin relative to deposition of the same benefit agent if it were not structured or not in presence of structured benefit agent;
   wherein said separately formed structured benefit agent is molten, semi-molten or solid at the time of combination with the carrying composition,
   wherein said carrying composition with which said structured benefit agent delivery vehicle is combined comprises said surfactant of (1), said structuring aid and/or filler of (3) and optional ingredients for personal cleansing bar
   wherein said process comprises:
   (1) mixing hydrophobic benefit agent or agents and structuring material at a temperature above the melting point of the structuring material, and then either cooling to ambient temperature so that it can be combined later with the bar carrying composition, or optionally cooling to the temperature at which the carrying composition is mixed before combining with the carrying composition;
   (2) combining said separately prepared premix and the carrying composition, optionally with mixing; and
   (3) pouring the resulting mixtures into molds and cooling to room temperature; or
   (4) cooling the resulting mixture to flakes, and extruding flakes so formed into a billet which may be formed and stamped.

2. A method of enhancing deposition of hydrophobic benefit agent comprising adding to skin or other substrate a personal product composition comprising:
   1) 1 to 80% surfactant; and
   2) 0.1 to 90% of a benefit agent delivery vehicle consisting essentially of;
      (a) 0.1 to 99.9% by wt. of structured benefit agent composition comprising one or more hydrophobic benefit agents or mixtures thereof; and
      (b) 99.9 to 0.1% structuring material wherein said structuring material is selected from the group consisting of paraffin, victory amber wax and mixtures thereof;
   3) 0.1 to 80% structuring aid and/or filler;
   wherein, when said structured benefit agent is separately formed and separately combined with or to a carrying composition in which the structured benefit agent will be used to deliver benefit agent onto skin there will be provided at least a 5% increase in deposition of benefit agent to the skin relative to deposition of the same benefit agent if not structured or not in the presence of structured benefit agent,
   wherein said separately formed structured benefit agent is molten, semi-molten or solid at the time of combination with the carrying compositions
   wherein said carrying composition with which said structured benefit agent delivery vehicle is combined comprises said surfactant of (1), said structuring aid and/or filler of (3) and optional ingredients for personal cleansing bar
   wherein said composition is made according to the process of claim 1.

3. A method of providing smooth feel comprising applying to skin or other substrate a personal product composition comprising:
   1) 1 to 80% surfactant; and
   2) 0.1 to 90% of a benefit agent vehicle consisting essentially of;
      (a) 0.1 to 99.9% by wt, of structured benefit agent composition of one or more hydrophobic benefit agents or mixtures thereof; and
      (b) 99.9 to 0.1% structuring material wherein said structuring material is selected from the group consisting of paraffin, victory amber wax and mixtures thereof,
   3) 0.1 to 80% structuring aid and/or filler;
   wherein, when said structured benefit agent is separately formed and separately combined with or to a carrying composition in which the structured benefit agent will be used to deliver benefit agent onto skin, there will be provided at least a 5% increase in deposition of benefit agent to the skin relative to deposition of the same benefit agent if not structured or not in the presence of structured benefit agent;
   wherein said separately formed structured benefit agent is molten semi-molten or solid at the time of combination with the carrying composition;
   wherein said carrying composition with which said structured benefit agent delivery vehicle is combined comprises said surfactant of (1), said structuring aid and/or filler of (3) and optional ingredients for personal cleansing bar
   wherein said composition is made according to the process of claim 1.

* * * * *